United States Patent
Lawandy

[11] Patent Number: 5,817,048
[45] Date of Patent: Oct. 6, 1998

[54] ULTRASONIC ALTERNATIVE TO LASER-BASED PHOTODYNAMIC THERAPY

[75] Inventor: Nabil M. Lawandy, North Kingston, R.I.

[73] Assignee: Brown University Research Foundation, Providence, R.I.

[21] Appl. No.: 821,088

[22] Filed: Mar. 20, 1997

[51] Int. Cl.[6] .................................................. A61N 1/30
[52] U.S. Cl. ................................................. 604/20; 604/22
[58] Field of Search ................................. 604/22; 128/20, 128/21, 890.1, 891.1, 892.1, DIG. 12, DIG. 13

*Primary Examiner*—Manuel Mendez
*Attorney, Agent, or Firm*—Perman & Green, LLP

[57] ABSTRACT

Disclosed is a method for activating photosensitive therapeutic and other compounds, comprising the steps of (a) providing a photosensitive therapeutic compound in combination with an appropriate solvent, such as dimethyl phthalate (DMP); (b) generating acoustic energy for generating free radicals from the solvent and reacting the free radicals with an oxalate ester to generate a key intermediate; (c) transferring chemical energy to the photosensitive therapeutic compound from the key intermediate; and (d) activating the photosensitive compound with the transferred energy. In an illustrative embodiment of this invention the oxalate ester is comprised of ester bis (2,4-dinitrophenyl) oxalate (DNPO). Also disclosed is a method for enhancing the effectiveness of photodynamic therapy by also generating acoustic energy to increase selectivity and/or increase the numbers of free radicals. In addition, an ultrasound-based therapy is described which uses a selectively retained or absorbed chemical species in conjunction with existing $O_2$ in the body to create reactive species such as $H_2O_2$ with ultrasonic excitation. It is also within the scope of this invention to increase the oxygen level of the blood stream and tissue prior to and during treatment, such as by using an ultrasound contrast agent.

15 Claims, 2 Drawing Sheets

ULTRASONIC ALTERNATIVE TO LASER-BASED PHOTODYNAMIC THERAPY

FIELD OF THE INVENTION

This invention relates generally to energy-activated therapeutic procedures.

BACKGROUND OF THE INVENTION

In the treatment of cancer and macular degeneration with photodynamic therapy (PDT), a class of photosensitizing compounds has been developed by a number of drug companies that are either selectively retained in, or are preferentially produced by, rapidly dividing cells. These dye-like molecules, when exposed to laser light in the visible or UV region, are excited to the triplet state where they have the capacity to promote molecular oxygen to its first excited singlet ($^1O_2$). This species of molecular oxygen is believed to be cytotoxic and to cause local necrosis of tumor cells. However, one particular drawback of the technique is the limit in penetration depth inherent in using visible light as an activation mechanism. Furthermore, treatment of internal cancer sites is necessarily invasive, requiring the use of fiber optic catheters, endoscopes, or similar instruments.

OBJECTS OF THE INVENTION

It is a first object of this invention to provide an improved method for activating photosensitive therapeutic and other chemical species, the improved method employing ultrasonic energy.

It is a further object of this invention to provide a non-invasive system for the in-vivo activation of a photosensitive therapeutic compounds.

SUMMARY OF THE INVENTION

The foregoing and other problems are overcome and the objects of the invention are realized by methods and apparatus in accordance with embodiments of this invention, wherein acoustic energy, in particular ultrasonic energy in the kilohertz to megahertz range (e.g., one kilohertz to 100 megahertz), is used to initiate the chemical pumping of a photodynamic therapy photosensitizer, such as protoporphyrin IX. The penetration of ultrasound into the human body makes the technique of this invention an attractive, non-invasive alternative to conventional photodynamic therapy.

Disclosed is a method for activating photosensitive therapeutic compounds and other chemical species, comprising the steps of (a) providing a photosensitive therapeutic compound in combination with an appropriate hydrogen containing solvent such as $H_2O$, dibutyl phthalate, ethyl acetate, and dimethyl phthalate (DMP); (b) generating acoustic energy for producing free radicals from the solvent and reacting the free radicals with an oxalate ester to generate a key intermediate; (c) transferring chemical energy to the photosensitive therapeutic compound from the key intermediate; and (d) activating the photosensitive compound with the transferred energy. In an illustrative embodiment of this invention the oxalate ester is comprised of ester bis (2,4-dinitrophenyl) oxalate (DNPO).

Also disclosed is a method for enhancing the effectiveness of photodynamic therapy by also generating acoustic energy to increase selectivity and/or increase the numbers of free radicals.

In addition, an ultrasound-based therapy is disclosed which uses a selectively retained or absorbed chemical species in conjunction with existing $O_2$ in the body to create reactive species such as $H_2O_2$ with ultrasonic excitation.

It is also within the scope of this invention to increase the $O_2$ level of the blood stream and tissue prior to and during treatment, such as by using an ultrasound contrast agent that generates microbubbles within the blood stream.

BRIEF DESCRIPTION OF THE DRAWINGS

The above set forth and other features of the invention are made more apparent in the ensuing Detailed Description of the Invention when read in conjunction with the attached Drawings, wherein.

DETAILED DESCRIPTION OF THE INVENTION

The inventor has realized that another activation pathway exists for the activation of photosensitive therapeutic compounds. In particular, the inventor has realized that acoustic energy, in particular ultrasound energy, can be used as an activation pathway, either instead of light or in combination with light.

The teaching of this invention has been shown to produce satisfactory results by applying ultrasound (ultrasonic) energy to, in the following example, peroxyoxalate chemiluminescent systems (PO CL). In these systems, oxalic acid derivatives react with hydrogen peroxide in the presence of a fluorophore to produce a bright emission characteristic of the fluorescer. This reaction proceeds via an energetic key intermediate, which is proposed to be 1,2-dioxetanedione.

Figure 1:
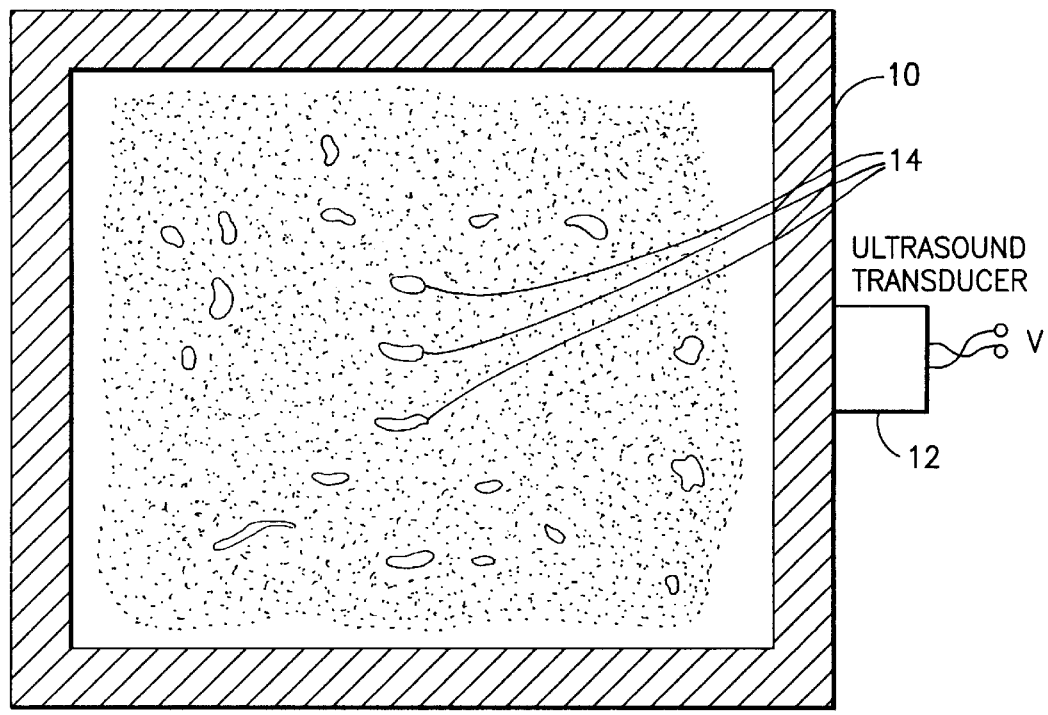
FIG. 1 depicts an ultrasound chamber and shows chemiluminescent emission from anti-nodes of an ultrasound field within the chamber.
Figure 2:
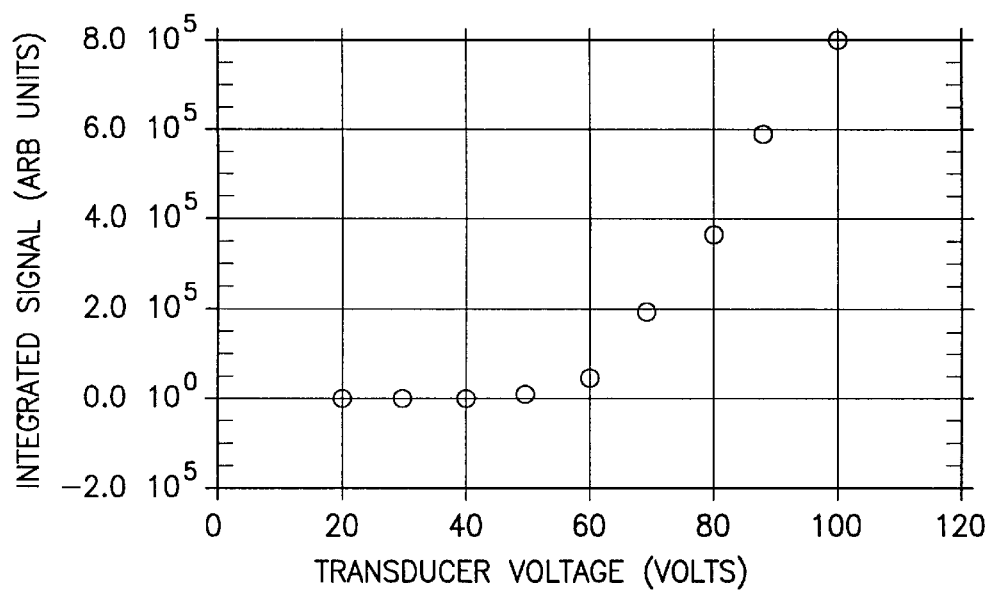
FIG. 2 is a graph that shows ultrasound-induced chemiluminescent intensity versus ultrasound transducer drive voltage, wherein the ultrasound energy is shown to be linear with voltage.

It was experimentally determined that light is produced at appreciable levels, without the addition of hydrogen peroxide, when the ester bis (2,4-dinitrophenyl) oxalate (DNPO) and the fluorescer rubrene in the solvent dimethyl phthalate (DMP) are sonicated with an ultrasound bath 10, having an ultrasound transducer 12 operated at 20 kHz. The ultrasound transducer 12 may generally be operated in the kilohertz to megahertz range. As is shown in FIG. 1, a greatest light intensity is observed at the antinodes 14 of the standing waves produced by the sonication bath. Additionally, the threshold behavior of the chemiluminescent intensity vs. ultrasound power (FIG. 2) suggests that the reactive species initiating the reaction is produced via weak micro-scale cavitation.

Through a calorimetric assay it was determined that the irradiation of pure DMP solvent with ultrasound produced hydrogen peroxide at a rate of $8.4 \times 10^{-5}$ M/min. Therefore, applying ultrasound to DMP with DNPO produces the key intermediate via the action of $H_2O_2$ on the ester.

As the key intermediate is capable of transferring energy of several eV to the fluorescer, it was recognized that this can be used as a pathway to activate PDT photosensitizers. That is, instead of transferring energy to a conventional fluorescer, the key intermediate is instead used to transfer energy to a selected PDT photosensitizer. In this manner the therapeutic action of the PDT compound can be realized without requiring light to be generated and delivered to the PDT compound.

In order to show that this pathway is valid, an experiment was performed with protoporphyrin IX (PpIX) dimethyl ether. When PpIX is irradiated in the presence of molecular oxygen, the singlet oxygen is produced and reacts back on the molecule producing several reaction products, the most common of which has a strong absorption peak at 670 nm. Therefore, the growth of this 670 nm peak is taken to indicate the production of $^1O_2$. When PpIX in DMP was sonicated, this peak was identified only when the ester DNPO was present, suggesting that the key intermediate produced by the action of ultrasound on DMP is leading to the production of $^1O_2$ through energy transfer to the PpIX molecule.

It has been shown that this result presents the possibility of a new modality for activating tumor-specific photosensitizers without the use of lasers or other light sources. It is believed that a similar mechanism is present under in vivo conditions. A selected source of free radicals and a PDT compound can be delivered to a site to be treated by accumulation in rapidly dividing cells or by antigen binding.

Figure 3:
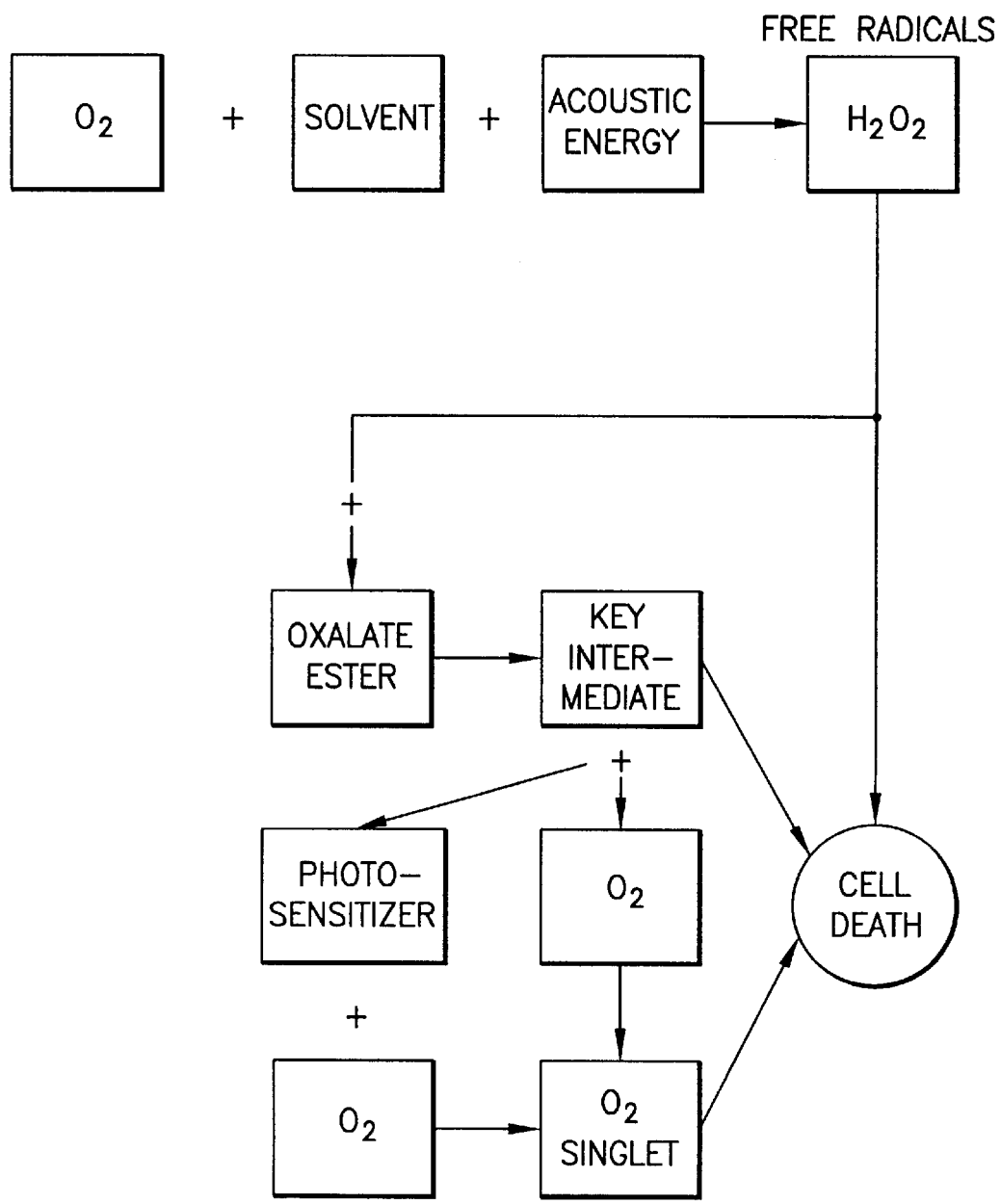
FIG. 3 illustrates a method of this invention.

Referring to FIG. 3, and in accordance with this invention, a combination of $O_2$ plus a hydrogen solvent, for example DMP, plus acoustic energy yields free radicals (e.g., $H_2O_2$). The presence of the free radicals results, in turn, in cell death. Assuming that the cells are targeted cells, such as rapidly dividing cells, the intended result is achieved.

In another pathway the $H_2O_2$ combines with an oxalate ester to yield a key intermediate. In one path the key intermediate itself results in cell death, while in another path the key intermediate plus $O_2$ yields the $O_2$ singlet, which results in cell death, while in yet another path the key intermediate plus a photosensitizer (e.g., Foscan, Photofrin, or Lu-Tex) plus $O_2$ yields the $O_2$ singlet, which results in cell death. The $O_2$ may be $O_2$ found in the body.

Other oxalate esters include the following.
Bis(2-nitrophenyl)
Bis(4-nitrophenyl)
Bis(4-nitro 3-trifluoromethyl)
Bis(4-nitro-2-formylphenyl)
Bis(4-nitro-2,6-dichlorophenyl)
Bis(2.4-dinitrophenyl)
Bis(2,5-dinitrophenyl)
Bis (2,4-dichlorophenyl)
Bis(pentacholorophenyl)
Bis(pentafluorophenyl)
Bis(3-trifluoro-methylphenyl)
Bis(3.5-di(trifluoro-methylphenyl)
Bis(2,6-dimethylphenyl)
Bis(4-methoxyphenyl)
Diphenyl
Phenylene
Bis(2-naphthyl)
Di-i-butyl
Bis(2-cyano-2-propyl)
Bis(2,2,2-trifluoro-ethyl)
Bis(diphenylmethyl)

Another oxalate ester of interest is bis(2,4,6-trichlorophenyl) oxalate.

This invention further teaches a combined use of acoustic energy with PDT to increase selectivity and/or enhance the effect of PDT by providing increased numbers of free radicals.

By example, PDT uses specifically designed drugs such as Foscan® (Scotia Pharmaceuticals), ALA (DUSA) and Photofrin (QLT Phototherapeutics) to destroy rapidly dividing cells. These drugs are selectively retained by lipoproteins or generated at rapidly dividing cells and are subsequently excited by light to produce the desired effects. The primary mode of activity usually involves energy transfer from the photoexcited drug to $O_2$ to produce superoxides or $O_2$ in its singlet state. This excitation is typically provided by a laser or lamp.

Two of the most important photodynamic therapy drugs are the naturally occurring ALA compound and Photofrin. Both of these are porphyrin compounds that have a peak absorption at 630 nm with a linewidth of approximately 35 nm.

In accordance with this aspect of the invention a method for performing photodynamic therapy includes the steps of (a) providing a desired photodynamic therapeutic compound; (b) irradiating the phototherapeutic compound with light having wavelengths that are absorbed by the photodynamic compound; and, in conjunction with irradiating the photodynamic compound, (c) enhancing the effectiveness of the photodynamic compound by generating acoustic energy in accordance with the foregoing teachings.

It is also within the scope of the teaching of this invention to increase the oxygen concentration of the blood or tissues prior to and during the application of acoustic energy.

By example, it is known to inject an emulsion into the blood stream to enhance ultrasound images made during an ultrasound scan. Such an emulsion is referred to as a contrast agent. One known emulsion for this purpose is based on the fluorocarbon dodecafluoropentane, and is referred to as EchoGen™ (Sonus Pharmaceuticals Inc.). After injection the emulsion changes from a liquid to a gas, and infuses the blood with microbubbles that are capable of traversing the lungs intact, and that are small enough to traverse capillaries that are 3 to 5 $\mu$m in diameter without damage. The microbubbles are exhaled through the lungs after a few moments. The microbubbles are about $10^5$ times more reflective than red blood cells to the ultrasound energy, and their presence serves to enhance the ultrasound image.

Referring again to FIG. 3, it can be seen that the presence of $O_2$ is an important element in the activation pathways that lead to targeted cell death. The use of a suitable contrast agent is thus beneficial for temporarily increasing the $O_2$ level of the blood or tissues during the execution of the methods of this invention. Other known types of techniques for increasing the $O_2$ level of a tissue to be treated can also be employed.

While the invention has been particularly shown and described with respect to preferred embodiments thereof, it will be understood by those skilled in the art that changes in form and details may be made therein without departing from the scope and spirit of the invention.

What is claimed is:

1. A method for activating photosensitive therapeutic and other compounds, comprising the steps of:
   (a) providing a photosensitive therapeutic compound in combination with a hydrogen-containing solvent;
   (b) generating acoustic energy for generating free radicals from the solvent and reacting the free radicals with an oxalate ester to generate a key intermediate;
   (c) transferring chemical energy to the photosensitive therapeutic compound from the key intermediate; and
   (d) activating the photosensitive compound with the transferred energy.

2. A method as set forth in claim 1, wherein the solvent is comprised of dimethyl phthalate (DMP).

3. A method as set forth in claim 1, wherein the oxalate ester is comprised of ester bis(2,4-dinitrophenyl) oxalate (DNPO).

4. A method as set forth in claim 1, wherein the oxalate ester is comprised of bis(2,4,6-trichlorophenyl) oxalate.

5. A method as set forth in claim 1, wherein the step of activating occurs in a living tissue, and further comprising an initial step of increasing an $O_2$ level of the tissue.

6. An apparatus for activating a photosensitive therapeutic compound, comprising:

an ultrasonic transducer having an output providing energy having a frequency within a predetermined range of frequencies, said output being coupled to a tissue to be treated for exciting a photosensitive therapeutic compound that is applied to the tissue to be treated, wherein the energy is used to generate chemical energy for activating the photosensitive therapeutic compound either alone or in combination with light.

7. A method for causing cell death, comprising steps of:

combining $O_2$, a solvent, and acoustic energy to yield free radicals;

combining the free radicals and an oxalate ester to generate a key intermediate;

in one path combining the key intermediate and $O_2$ to yield the $O_2$ singlet, and using the $O_2$ singlet to cause cell death; and in the another path, using the key intermediate to cause cell death.

8. A method as set forth in claim 7, wherein in another path the method includes steps of combining the key intermediate, a photosensitizer, and $O_2$ to yield the $O_2$ singlet, and using the $O_2$ singlet to cause cell death.

9. A method as set forth in claim 7, wherein the free radicals are comprised of $H_2O_2$, and wherein the free radicals are also used to cause cell death.

10. A method as set forth in claim 7, wherein the solvent is comprised of dimethyl phthalate (DMP).

11. A method as set forth in claim 7, and further comprising an initial step of increasing an $O_2$ level of a tissue wherein cell death is to occur.

12. A method as set forth in claim 11, wherein the step of increasing the $O_2$ level includes a step of generating microbubbles within the blood stream.

13. A method for performing photodynamic therapy, comprising steps of:

providing a photodynamic therapeutic compound at a tissue;

irradiating the photodynamic therapeutic compound with light having wavelengths that are absorbed by the photodynamic compound;

in conjunction with irradiating the photodynamic therapeutic compound, enhancing the effectiveness of the photodynamic therapeutic compound by generating acoustic energy for generating free radicals and reacting the free radicals with an oxalate ester to generate a key intermediate; and transferring chemical energy to the photosensitive therapeutic compound from the key intermediate.

14. A method as set forth in claim 13, wherein the step of generating acoustic energy includes an initial step of increasing an $O_2$ level of the tissue.

15. A method as set forth in claim 14, wherein the step of increasing the $O_2$ level includes a step of generating microbubbles within the blood stream.

* * * * *